(12) United States Patent
Waynik et al.

(10) Patent No.: US 8,165,658 B2
(45) Date of Patent: Apr. 24, 2012

(54) METHOD AND APPARATUS FOR POSITIONING A GUIDE RELATIVE TO A BASE

(75) Inventors: Jeffrey M. Waynik, Nederland, CO (US); Andrew N. Csavoy, Minneapolis, MN (US); Keith Sootsman, Kalamazoo, MI (US); Matthew S. Solar, Indialantic, FL (US); Thomas I. Miller, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 810 days.

(21) Appl. No.: 12/239,114

(22) Filed: Sep. 26, 2008

(65) Prior Publication Data

US 2010/0081914 A1    Apr. 1, 2010

(51) Int. Cl.
*A61B 5/05* (2006.01)

(52) U.S. Cl. ........ 600/426; 600/407; 600/424; 600/429; 606/130

(58) Field of Classification Search .................. 600/407, 600/424, 426, 429; 606/130
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |

(Continued)

FOREIGN PATENT DOCUMENTS

CA    964149 A1    3/1975

(Continued)

OTHER PUBLICATIONS

International Search Report and Written Opinion mailed Apr. 11, 2009 for PCT/US2009/051341 filed Jul. 22, 2009.

(Continued)

*Primary Examiner* — Brian Casler
*Assistant Examiner* — Joel Lamprecht
(74) *Attorney, Agent, or Firm* — Scott A. Marks; Harness Dickey & Pierce PLC

(57) ABSTRACT

A system for positioning a guide relative to an anatomy is provided. The system can include a base adapted to be coupled to the anatomy, and a guide that can move relative to the base. The system can include at least one tracking device that can be coupled to the base and the guide, and a tracking system that tracks a position of the tracking device. The system can include a navigation system that determines a position of the base and the guide relative to the anatomy, and whether the position of the base and the guide are in a desired position. The system can include a display, which can display at least one icon superimposed on the image of the anatomy that graphically indicates a manipulation of the guide required to move the guide into the desired position.

26 Claims, 4 Drawing Sheets

U.S. PATENT DOCUMENTS

| | | | |
|---|---|---|---|
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |

| Patent No. | Date | Name |
|---|---|---|
| 5,117,836 A | 6/1992 | Millar |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,484,437 A | 1/1996 | Michelson |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,531,673 A | 7/1996 | Helenowski |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,558,638 A | 9/1996 | Evers et al. |
| 5,566,681 A | 10/1996 | Manwaring et al. |
| 5,568,384 A | 10/1996 | Robb et al. |
| 5,568,809 A | 10/1996 | Ben-haim |
| 5,571,109 A | 11/1996 | Bertagnoli et al. |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |

| | | | | | | |
|---|---|---|---|---|---|---|
| 5,590,215 A | 12/1996 | Allen | | 5,795,294 A | 8/1998 | Luber et al. |
| 5,592,939 A | 1/1997 | Martinelli | | 5,797,849 A | 8/1998 | Vesely et al. |
| 5,595,193 A | 1/1997 | Walus et al. | | 5,799,055 A | 8/1998 | Peshkin et al. |
| 5,596,228 A | 1/1997 | Anderton et al. | | 5,799,099 A | 8/1998 | Wang et al. |
| 5,600,330 A | 2/1997 | Blood | | 5,800,352 A | 9/1998 | Ferre et al. |
| 5,603,318 A | 2/1997 | Heilbrun et al. | | 5,800,535 A | 9/1998 | Howard, III |
| 5,611,025 A | 3/1997 | Lorensen et al. | | 5,802,719 A | 9/1998 | O'Farrell, Jr. et al. |
| 5,617,462 A | 4/1997 | Spratt | | 5,803,089 A | 9/1998 | Ferre et al. |
| 5,617,857 A | 4/1997 | Chader et al. | | 5,807,252 A | 9/1998 | Hassfeld et al. |
| 5,619,261 A | 4/1997 | Anderton | | 5,810,008 A | 9/1998 | Dekel et al. |
| 5,622,169 A | 4/1997 | Golden et al. | | 5,810,728 A | 9/1998 | Kuhn |
| 5,622,170 A | 4/1997 | Schulz | | 5,810,735 A | 9/1998 | Halperin et al. |
| 5,627,873 A | 5/1997 | Hanover et al. | | 5,820,553 A | 10/1998 | Hughes |
| 5,628,315 A | 5/1997 | Vilsmeier et al. | | 5,823,192 A | 10/1998 | Kalend et al. |
| 5,630,431 A | 5/1997 | Taylor | | 5,823,958 A | 10/1998 | Truppe |
| 5,636,644 A | 6/1997 | Hart et al. | | 5,824,048 A | 10/1998 | Tuch |
| 5,638,819 A | 6/1997 | Manwaring et al. | | 5,828,725 A | 10/1998 | Levinson |
| 5,640,170 A | 6/1997 | Anderson | | 5,828,770 A | 10/1998 | Leis et al. |
| 5,642,395 A | 6/1997 | Anderton et al. | | 5,829,444 A | 11/1998 | Ferre et al. |
| 5,643,268 A | 7/1997 | Vilsmeier et al. | | 5,831,260 A | 11/1998 | Hansen |
| 5,645,065 A | 7/1997 | Shapiro et al. | | 5,833,608 A * | 11/1998 | Acker .......................... 600/409 |
| 5,646,524 A | 7/1997 | Gilboa | | 5,834,759 A | 11/1998 | Glossop |
| 5,647,361 A | 7/1997 | Damadian | | 5,836,954 A | 11/1998 | Heilbrun et al. |
| 5,662,111 A | 9/1997 | Cosman | | 5,840,024 A | 11/1998 | Taniguchi et al. |
| 5,664,001 A | 9/1997 | Tachibana et al. | | 5,840,025 A | 11/1998 | Ben-Haim |
| 5,674,296 A | 10/1997 | Bryan et al. | | 5,843,076 A | 12/1998 | Webster, Jr. et al. |
| 5,676,673 A | 10/1997 | Ferre et al. | | 5,848,967 A | 12/1998 | Cosman |
| 5,681,260 A | 10/1997 | Ueda et al. | | 5,851,183 A | 12/1998 | Bucholz |
| 5,682,886 A | 11/1997 | Delp et al. | | 5,865,846 A | 2/1999 | Bryan et al. |
| 5,682,890 A | 11/1997 | Kormos et al. | | 5,868,674 A | 2/1999 | Glowinski et al. |
| 5,690,108 A | 11/1997 | Chakeres | | 5,868,675 A | 2/1999 | Henrion et al. |
| 5,690,117 A | 11/1997 | Gilbert | | 5,871,445 A | 2/1999 | Bucholz |
| 5,694,945 A | 12/1997 | Ben-Haim | | 5,871,455 A | 2/1999 | Ueno |
| 5,695,500 A | 12/1997 | Taylor et al. | | 5,871,487 A | 2/1999 | Warner et al. |
| 5,695,501 A | 12/1997 | Carol et al. | | 5,873,822 A | 2/1999 | Ferre et al. |
| 5,696,500 A | 12/1997 | Diem | | 5,882,304 A | 3/1999 | Ehnholm et al. |
| 5,697,377 A | 12/1997 | Wittkampf | | 5,884,410 A | 3/1999 | Prinz |
| 5,702,406 A | 12/1997 | Vilsmeier et al. | | 5,889,834 A | 3/1999 | Vilsmeier et al. |
| 5,711,299 A | 1/1998 | Manwaring et al. | | 5,891,034 A | 4/1999 | Bucholz |
| 5,713,946 A | 2/1998 | Ben-Haim | | 5,891,157 A | 4/1999 | Day et al. |
| 5,715,822 A | 2/1998 | Watkins et al. | | 5,904,691 A | 5/1999 | Barnett et al. |
| 5,715,836 A | 2/1998 | Kliegis et al. | | 5,907,395 A | 5/1999 | Schulz et al. |
| 5,718,241 A | 2/1998 | Ben-Haim et al. | | 5,913,820 A | 6/1999 | Bladen et al. |
| 5,727,552 A | 3/1998 | Ryan | | 5,920,395 A | 7/1999 | Schulz |
| 5,727,553 A | 3/1998 | Saad | | 5,921,992 A | 7/1999 | Costales et al. |
| 5,729,129 A | 3/1998 | Acker | | 5,923,727 A | 7/1999 | Navab |
| 5,730,129 A | 3/1998 | Darrow et al. | | 5,928,248 A | 7/1999 | Acker |
| 5,730,130 A | 3/1998 | Fitzpatrick et al. | | 5,938,603 A | 8/1999 | Ponzi |
| 5,732,703 A | 3/1998 | Kalfas et al. | | 5,938,694 A | 8/1999 | Jaraczewski et al. |
| 5,733,259 A | 3/1998 | Valcke et al. | | 5,947,980 A | 9/1999 | Jensen et al. |
| 5,735,278 A | 4/1998 | Hoult et al. | | 5,947,981 A | 9/1999 | Cosman |
| 5,735,814 A | 4/1998 | Elsberry et al. | | 5,950,629 A | 9/1999 | Taylor et al. |
| 5,738,096 A | 4/1998 | Ben-Haim | | 5,951,475 A | 9/1999 | Gueziec et al. |
| 5,740,802 A | 4/1998 | Nafis et al. | | 5,951,571 A | 9/1999 | Audette |
| 5,740,808 A | 4/1998 | Panescu et al. | | 5,954,647 A | 9/1999 | Bova et al. |
| 5,741,214 A | 4/1998 | Ouchi et al. | | 5,954,796 A | 9/1999 | McCarty et al. |
| 5,742,394 A | 4/1998 | Hansen | | 5,957,844 A | 9/1999 | Dekel et al. |
| 5,744,953 A | 4/1998 | Hansen | | 5,967,980 A | 10/1999 | Ferre et al. |
| 5,748,767 A | 5/1998 | Raab | | 5,967,982 A | 10/1999 | Barnett |
| 5,749,362 A | 5/1998 | Funda et al. | | 5,968,047 A | 10/1999 | Reed |
| 5,749,835 A | 5/1998 | Glantz | | 5,970,499 A | 10/1999 | Smith et al. |
| 5,752,513 A | 5/1998 | Acker et al. | | 5,971,997 A | 10/1999 | Guthrie et al. |
| 5,755,725 A | 5/1998 | Druais | | 5,976,156 A | 11/1999 | Taylor et al. |
| RE35,816 E | 6/1998 | Schulz | | 5,980,535 A | 11/1999 | Barnett et al. |
| 5,758,667 A | 6/1998 | Slettenmark | | 5,983,126 A | 11/1999 | Wittkampf et al. |
| 5,762,064 A | 6/1998 | Polvani | | 5,987,349 A | 11/1999 | Schulz |
| 5,767,669 A | 6/1998 | Hansen et al. | | 5,987,960 A | 11/1999 | Messner et al. |
| 5,767,699 A | 6/1998 | Bosnyak et al. | | 5,999,837 A | 12/1999 | Messner et al. |
| 5,767,960 A | 6/1998 | Orman | | 5,999,840 A | 12/1999 | Grimson et al. |
| 5,769,789 A | 6/1998 | Wang et al. | | 6,001,130 A | 12/1999 | Bryan et al. |
| 5,769,843 A | 6/1998 | Abela et al. | | 6,006,126 A | 12/1999 | Cosman |
| 5,769,861 A | 6/1998 | Vilsmeier | | 6,006,127 A | 12/1999 | Van Der Brug et al. |
| 5,772,594 A | 6/1998 | Barrick | | 6,013,087 A | 1/2000 | Adams et al. |
| 5,772,661 A | 6/1998 | Michelson | | 6,014,580 A | 1/2000 | Blume et al. |
| 5,775,322 A | 7/1998 | Silverstein et al. | | 6,016,439 A | 1/2000 | Acker |
| 5,776,064 A | 7/1998 | Kalfas et al. | | 6,019,725 A | 2/2000 | Vesely et al. |
| 5,782,765 A | 7/1998 | Jonkman | | 6,024,695 A | 2/2000 | Taylor et al. |
| 5,787,886 A | 8/1998 | Kelly et al. | | 6,026,316 A | 2/2000 | Kucharczyk et al. |
| 5,792,055 A | 8/1998 | McKinnon | | 6,050,724 A | 4/2000 | Schmitz et al. |

| | | | |
|---|---|---|---|
| 6,059,718 A | 5/2000 | Taniguchi et al. |
| 6,063,022 A | 5/2000 | Ben-Haim |
| 6,064,904 A | 5/2000 | Yanof et al. |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,194,639 B1 | 2/2001 | Botella et al. |
| 6,198,794 B1 | 3/2001 | Peshkin et al. |
| 6,201,387 B1 | 3/2001 | Govari |
| 6,203,497 B1 | 3/2001 | Dekel et al. |
| 6,206,885 B1 | 3/2001 | Ghahremani et al. |
| 6,211,666 B1 | 4/2001 | Acker |
| 6,223,067 B1 | 4/2001 | Vilsmeier et al. |
| 6,233,476 B1 | 5/2001 | Strommer et al. |
| 6,246,231 B1 | 6/2001 | Ashe |
| 6,259,942 B1 | 7/2001 | Westermann et al. |
| 6,273,896 B1 | 8/2001 | Franck et al. |
| 6,283,951 B1 | 9/2001 | Flaherty et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,332,089 B1 | 12/2001 | Acker et al. |
| 6,341,231 B1 | 1/2002 | Ferre et al. |
| 6,348,058 B1 | 2/2002 | Melkent et al. |
| 6,351,659 B1 | 2/2002 | Vilsmeier |
| 6,381,485 B1 | 4/2002 | Hunter et al. |
| 6,385,483 B1 | 5/2002 | Uber, III et al. |
| 6,390,097 B1 | 5/2002 | Chandra |
| 6,402,689 B1 | 6/2002 | Scarantino et al. |
| 6,406,426 B1 | 6/2002 | Reuss et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,464,662 B1 | 10/2002 | Raghavan et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,482,182 B1 | 11/2002 | Carroll et al. |
| 6,484,049 B1 | 11/2002 | Seeley et al. |
| 6,490,475 B1 | 12/2002 | Seeley et al. |
| 6,491,699 B1 | 12/2002 | Henderson et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,516,212 B1 | 2/2003 | Bladen et al. |
| 6,526,415 B2 | 2/2003 | Smith et al. |
| 6,527,443 B1 | 3/2003 | Vilsmeier et al. |
| 6,531,152 B1 | 3/2003 | Lerner et al. |
| 6,549,803 B1 | 4/2003 | Raghavan et al. |
| 6,551,325 B2 | 4/2003 | Neubauer et al. |
| 6,567,690 B2 | 5/2003 | Giller et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,658,396 B1 | 12/2003 | Tang et al. |
| 6,671,538 B1 | 12/2003 | Ehnholm et al. |
| 6,694,162 B2 | 2/2004 | Hartlep et al. |
| 6,701,179 B1 | 3/2004 | Martinelli et al. |
| 6,740,883 B1 | 5/2004 | Stodilka et al. |
| 6,755,789 B2 | 6/2004 | Stringer et al. |
| 6,828,966 B1 | 12/2004 | Gavriliu et al. |
| 6,901,287 B2 | 5/2005 | Davis et al. |
| 6,973,718 B2 | 12/2005 | Sheppard, Jr. et al. |
| 6,979,348 B2 | 12/2005 | Sundar |
| 6,982,282 B2 | 1/2006 | Lambert et al. |
| 7,011,814 B2 | 3/2006 | Suddarth et al. |
| 7,047,235 B2 | 5/2006 | Yang et al. |
| 7,072,705 B2 | 7/2006 | Miga et al. |
| 7,092,748 B2 | 8/2006 | Valdes Sosa et al. |
| 7,103,399 B2 | 9/2006 | Miga et al. |
| 7,167,180 B1 | 1/2007 | Shibolet |
| 7,194,295 B2 | 3/2007 | Vilsmeier |
| 7,313,430 B2 | 12/2007 | Urquhart et al. |
| 7,599,730 B2 | 10/2009 | Hunter et al. |
| 2001/0007918 A1 | 7/2001 | Vilsmeier et al. |
| 2002/0095081 A1 | 7/2002 | Vilsmeier et al. |
| 2003/0078485 A1 | 4/2003 | Hartlep |
| 2003/0101081 A1 | 5/2003 | Putnam et al. |
| 2003/0114752 A1 | 6/2003 | Henderson et al. |
| 2003/0191408 A1 | 10/2003 | Montgomery |
| 2004/0024309 A1 | 2/2004 | Ferre et al. |
| 2004/0039259 A1 | 2/2004 | Krause et al. |
| 2004/0068172 A1 | 4/2004 | Nowinski et al. |
| 2004/0092809 A1 | 5/2004 | DeCharms |
| 2004/0097806 A1 | 5/2004 | Hunter et al. |
| 2004/0107210 A1 | 6/2004 | Yang et al. |
| 2004/0138551 A1 | 7/2004 | Hartlep et al. |
| 2004/0158313 A1 | 8/2004 | Altman |
| 2004/0210124 A1 | 10/2004 | Nowinski et al. |
| 2004/0215071 A1 | 10/2004 | Frank et al. |
| 2004/0215162 A1 | 10/2004 | Putz |
| 2004/0236554 A1 | 11/2004 | Raghavan et al. |
| 2004/0240753 A1 | 12/2004 | Hu et al. |
| 2005/0002918 A1 | 1/2005 | Strauss et al. |
| 2005/0004617 A1 | 1/2005 | Dawant et al. |
| 2005/0018885 A1 | 1/2005 | Chen et al. |
| 2005/0031210 A1 | 2/2005 | Shen et al. |
| 2005/0049486 A1 | 3/2005 | Urquhart et al. |
| 2005/0070781 A1 | 3/2005 | Dawant et al. |
| 2005/0084146 A1 | 4/2005 | Watson et al. |
| 2005/0085714 A1 | 4/2005 | Foley et al. |
| 2005/0085720 A1 | 4/2005 | Jascob et al. |
| 2005/0101855 A1 | 5/2005 | Miga et al. |
| 2005/0111621 A1 | 5/2005 | Riker et al. |
| 2005/0148859 A1 | 7/2005 | Miga et al. |
| 2005/0171558 A1 | 8/2005 | Abovitz et al. |
| 2005/0245814 A1 | 11/2005 | Anderson et al. |
| 2006/0017749 A1 | 1/2006 | McIntyre et al. |
| 2006/0084867 A1 | 4/2006 | Tremblay et al. |
| 2006/0182321 A1 | 8/2006 | Hu et al. |
| 2006/0217733 A1 | 9/2006 | Plassky et al. |
| 2007/0021668 A1 | 1/2007 | Boese et al. |
| 2008/0081982 A1 | 4/2008 | Simon et al. |

FOREIGN PATENT DOCUMENTS

| | | |
|---|---|---|
| DE | 3042343 A1 | 6/1982 |
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 T0 | 11/2002 |
| EP | 0062941 | 10/1982 |
| EP | 0119660 A1 | 9/1984 |
| EP | 0155857 | 9/1985 |
| EP | 0319844 | 6/1989 |
| EP | 0326768 A2 | 8/1989 |
| EP | 0350996 A1 | 1/1990 |
| EP | 0419729 A1 | 4/1991 |
| EP | 0427358 | 5/1991 |
| EP | 0456103 | 11/1991 |

| | | | |
|---|---|---|---|
| EP | 0469966 A1 | 2/1992 |
| EP | 0581704 A1 | 2/1994 |
| EP | 0651968 A1 | 5/1995 |
| EP | 0655138 A1 | 5/1995 |
| EP | 0894473 A2 | 2/1999 |
| EP | 0908146 A2 | 4/1999 |
| EP | 0930046 A2 | 7/1999 |
| EP | 1306050 | 5/2003 |
| EP | 1344187 | 9/2003 |
| EP | 1396233 | 3/2004 |
| EP | 1406203 | 4/2004 |
| EP | 1442715 A2 | 8/2004 |
| EP | 1474782 | 11/2004 |
| EP | 1597701 | 11/2005 |
| EP | 1603076 | 12/2005 |
| EP | 1691687 | 8/2006 |
| EP | 1692633 | 8/2006 |
| EP | 1692657 | 8/2006 |
| EP | 1713015 | 10/2006 |
| FR | 2417970 A1 | 9/1979 |
| FR | 2618211 | 1/1989 |
| GB | 2094590 A | 9/1982 |
| GB | 2164856 A | 4/1986 |
| JP | 62327 | 6/1983 |
| JP | 61-94639 A | 10/1984 |
| JP | 63240851 A | 10/1988 |
| JP | 2765738 T | 4/1991 |
| JP | 3267054 | 11/1991 |
| WO | WO-8809151 A1 | 12/1988 |
| WO | WO-8905123 | 6/1989 |
| WO | WO-9005494 A1 | 5/1990 |
| WO | WO-9103982 A1 | 4/1991 |
| WO | WO-9104711 A1 | 4/1991 |
| WO | WO-9107726 A1 | 5/1991 |
| WO | WO-9203090 A1 | 3/1992 |
| WO | WO-9206645 A1 | 4/1992 |
| WO | WO-9404938 A1 | 3/1994 |
| WO | WO-9423647 A1 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |
| WO | WO-9838908 A1 | 9/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |
| WO | WO-9952094 A1 | 10/1999 |
| WO | WO-9960939 A1 | 12/1999 |
| WO | WO-0007652 | 2/2000 |
| WO | WO-0010034 | 2/2000 |
| WO | WO-0130437 A1 | 5/2001 |
| WO | WO-0243003 | 5/2002 |
| WO | WO-02093292 | 11/2002 |
| WO | WO-02097735 | 12/2002 |
| WO | WO-02098292 | 12/2002 |
| WO | WO-03039600 A1 | 5/2003 |
| WO | WO-03060827 | 7/2003 |
| WO | WO-2004077359 | 9/2004 |
| WO | WO-2004096018 | 11/2004 |
| WO | WO-2005002444 | 1/2005 |
| WO | WO-2005048844 | 6/2005 |
| WO | WO-2005052838 | 6/2005 |
| WO | WO-2005057493 | 6/2005 |
| WO | WO-2005057498 | 6/2005 |
| WO | WO-2005084542 | 9/2005 |
| WO | WO-2005096227 | 10/2005 |
| WO | WO-2005111931 | 11/2005 |
| WO | WO-2006011850 | 2/2006 |
| WO | WO-2006017053 | 2/2006 |
| WO | WO-2006017392 | 2/2006 |
| WO | WO-2006028416 | 3/2006 |
| WO | WO-2006028474 | 3/2006 |
| WO | WO-2006069250 | 6/2006 |
| WO | WO-2006083236 | 8/2006 |
| WO | WO-2006088429 | 8/2006 |

OTHER PUBLICATIONS

"Correction of Image Intensifier Distortion for Three-Dimensional Reconstruction," Presented at SPIE Medical Imaging, B. Schuele, et al. San Diego, California, 1995.

G. Champleboux, et al., "Accurate Calibration of Cameras and Range Imaging Sensors: the NPBS Method," Proceedings of the IEEE International Conference on Robotics and Automation, Nice, France, May 1992.

International Preliminary Report on Patentability for PCT/US2007/009931 mailed Jan. 20, 2009, claiming priority to U.S. Appl. No. 11/683,796, filed Mar. 8, 2007.

International Search Report and Written Opinion for PCT/US2007/009931 mailed Nov. 14, 2007, claiming priority to U.S. Appl. No. 11/683,796, filed Mar. 8, 2007.

iPlan® Stereotaxy Software, BrainLab, http://www.brainlab.com/scripts/website_english.asp?menuDeactivate=1&articleID=1842&articleTypeID=27&pageTypeID=4&article_short_headline=iPlan%AE%20Stereotaxy printed Apr. 1, 2009.

NeuroSight™ Cranial Module, Radionics™, Jul. 27, 2003 http://www.radionics.com/products/frameless/omnisight/omnisight_modules.shtml#neuro accessed and printed on Apr. 1, 2009 through the Wayback Machine at http://www.archive.org/web/web.php.

VectorVision® cranial Navigation Software, BrainLab, http://www.brainlab.com/scripts/website_english.asp?menuDeactivate=1&articleID=593&articleTypeID=27&pageTypeID=4&article_short_headline=VectorVision%AE%20%20cranial printed Apr. 1, 2009.

Versweyveld, Leslie, "Scientists in Singapore develop Virtual Brain Bench for stereotactic frame neurosurgery," VMW Virtual Medical Worlds Monthly, printed Apr. 1, 2009 (3 pages).

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 4, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensional Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Brown, R., M.D., A Stereotactic Head Frame for Use with CT Body Scanners, Investigative Radiology © J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164, (May 1, 1997) pp. 137-145.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. '96, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13 (1994) pp. 193-211.

Hamadeh et al, "Kinematic Study of Lumbar Spine Using Functional Radiographies and 3D/2D Registration," TIMC UMR 5525—IMAG (1997).

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Homer et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51 (1996) pp. 635-638.

Kosugi, Y., et al., An Articulated Neurosurgical Navigation System Using MRI and CT Images, IEEE Trans. on Biomed. Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble (1995).

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 926-927.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 430-431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al., "Computer Assisted Spine Surgery", Clinical Assisted Spine Surgery, No. 337 (1997) pp. 86-96.

Ng, W.S. et al., Robotic Surgery—A First-Hand Experience in Transurethral Resection of the Prostate Surgery, IEEE Eng. in Med. and Biology, pp. 120-125 (Mar. 1993).

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery (1996) pp. 329-341.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS (1995) pp. 185-192.

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images" (1997) pp. 119-128.

"Advanced Drug Delivery: Technologies, Applications & Markets Jul. 2003, A Kalorama Information Market Intelligence Report." (Jul. 2003) Kalorama Information 432 sheets.

"Interventional Radiology Grand Rounds. Topic: Central Venous Access." Society of Interventional Radiology, (2004) 4 sheets.

Arndt, "Neopharm Investigators Present Final Results of Peritumoral vs. Intratumoral Infusion of IL13-PE38QQR from Phase1 Clinical Studies at the American Society of Clinical Oncology Meeting." NeoPharm. Biowire2k 4st Annual Meeting of the American Society of Clinical Oncology. Business Wire (May 17, 2005) www.businesswire.com/news/home/20050517005098/en/NeoPharm-Investigators-Pr accessed Jul. 27, 2011.

Beghetto, M.G., et al. Parenteral Nutrition as a Risk Factor for Central Venous Catheter-Related Infection. Journal of Parenteral and Enteral Nutrition 29(5): (Sep. 4, 2005) pp. 367-373. http://www.redorbit.com/news/health/229618/parenteral_nutrition_as_a_risk_factor_for_central_venous_catheter/ (accessed Jul. 27, 2011).

Finnis, Kirk W., et al., "Three-Dimensional Database of Subcortical Electrophysiology for Image-Guided Stereotactic Functional Neurosurgery," IEEE Transactions of Medical Imaging, vol. 22, No. 1 (Jan. 2003) pp. 93-104.

Flanigan, M. et al.. Peritoneal Catheters and Exit-Site Practices Toward Optimum Peritoneal Access: A Review of Current Developments. Peritoneal Dialysis International. (2005) vol. 25, pp. 132-139.

Fletcher, S.J., et al. "Editorial II. Safe placement of central venous catheters: where should the tip of the catheter lie?" Oxford Journals, British Journal of Anaesthesia (2000) vol. 85 Issue 2, August. pp. 188-191.

Hanas, M.D., Ragnar. "Indwelling_Catheters_for_Injections. How to Reduce Injection Anxiety. Insuflon." (Jun. 2003) Children with Diabetes. http://www.childrenwithdiabetes.com/d_06_311.htm web accessed Jul. 27, 2011.

Hayashi, Y., et al. "Optimal Placement of CVP Catheter in Paediatric Cardiac Patients." Canadian Journal of Anesthesia, (1995) 42:6 pp. 479-482.

Hodge, D. et al. "Diagnosis, prevention, and management of catheter related bloodstream infection during long term parenteral nutrition." Arch. Dis. Child. Fetal Neonatal Ed. (2002) vol. 87 pp. F21-F24.

Hoenecke, Heinz, R., et al. "Continuous Local Anesthetic Infiltration," Case Report. Orthopedic Technology Review (Mar./Apr. 2002) vol. 3 No. 2. http://www.orthopedictechreview.com/issues/marapr02/case.htm. Said url is no longer valid. The article can be found using the Wayback Machine archive at: http://web.archive.org/web/20060315052636/http://www.orthopedictechreview.com/issues/marapr02/case.htm. Accessed and printed Aug. 11, 2011.

Kunwar, S., et al. "Peritumoral convection-enhanced delivery (CED) of IL13-PE38QQR (IL13PE): Results of multicenter phase 1 studies in recurrent High Grade Glioma (HGG)." Abstracts from the World Federation of Neuro-Oncology Second Quadrennial Meeting and Sixth Meeting of the European Association for Neuro-Oncology, Edinburgh, UK. (May 5-8, 2005) p. 311 Society for Neuro-Oncology.

Müller, M., et al. "Issues in Pharmacokinetics and Pharmacodynamics of Anti-Infective Agents: Distribution in Tissue." Antimicrobial Agents and Chemotherapy, MINIREVIEW (2004) vol. 48, No. 5. pp. 1441-1453.

Renard, E., et. al. "Catheter Complications Associated with Implantable Systems for Peritoneal Insulin Delivery. An Analysis of Frequency, Predisposing Factors, and Obstructing Materials." Diabetes Care (Mar. 1995) vol. 18, No. 3. pp. 300-306.

Vande Walle, et al. "Use of Bicarbonate/Lactate Buffered Dialysate with Nighttime Cycler, Associated with a Daytime Dwell with Icodextrin, May Result in Alkalosis in Children." Advances in Peritoneal Dialysis (2004) vol. 20, pp. 222-225.

Vesely, T.M., "Central Venous Catheter Tip Position: A Continuing Controversy." J Vasc Interv Radiol (2003) vol. 14, No. 5. pp. 527-534.

Washburn, Kimberly, K, et al. "Surgical Technique for Peritoneal Dialysis Catheter Placement in the Pediatric Patient: A North American Survey." Advances in Peritoneal Dialysis (2004) vol. 20, pp. 218-221.

Zürcher, Matthias et al. "Colonization and Bloodstream Infection with Single-Versus Multi-Lumen Central Venous Catheters: A Quantitative Systematic Review." Anesthesia & Analgesia (2004) vol. 99, pp. 177-182.

* cited by examiner

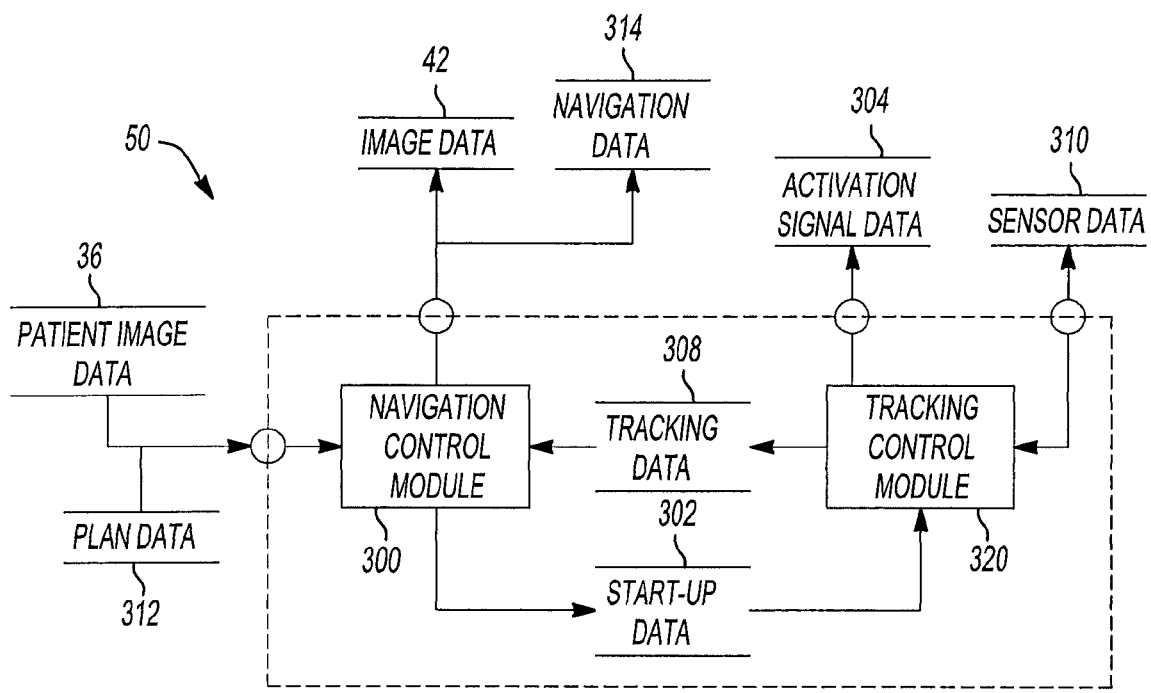
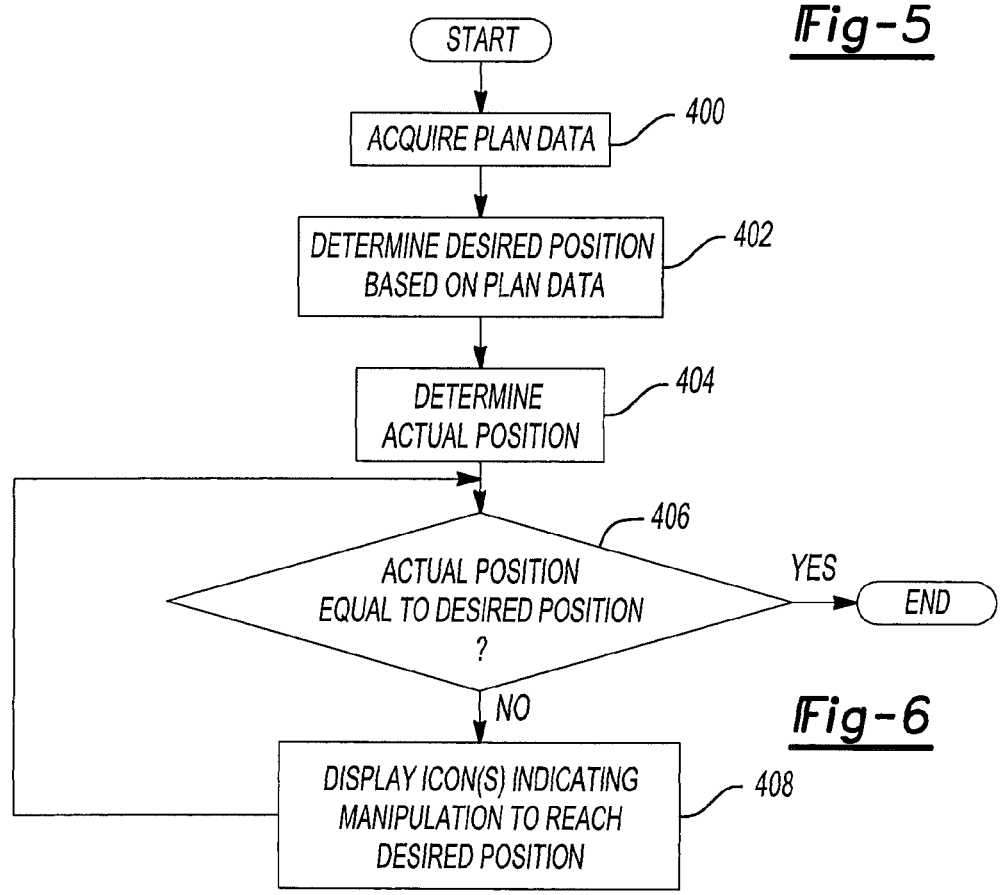

METHOD AND APPARATUS FOR POSITIONING A GUIDE RELATIVE TO A BASE

FIELD

The present disclosure relates to a surgical navigation system, and particularly to a method and apparatus for positioning a guide relative to a base.

BACKGROUND

The statements in this section merely provide background information related to the present disclosure and may not constitute prior art.

Image guided medical and surgical procedures utilize patient images (image data) obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in navigated medical procedures.

Generally, during a navigated procedure, images are acquired by a suitable imaging device for display on a workstation. The navigation system tracks the patient, instruments and other devices in the surgical field or patient space. These tracked devices are then displayed relative to the image data on the workstation in image space. In order to track the patient, instruments and other devices, the patient, instruments and other devices can be equipped with tracking devices.

SUMMARY

During a navigated procedure, a dynamic reference frame (DRF) including a tracking device can be fixed relative to the patient in order to track the patient. In addition, it may be desirable to use a holder, such as a screw, head frame, etc. to couple the tracking device to the patient. In some cases, the holder can comprise one or more parts, such as in the case of a head frame. Generally, the head frame can include a positionable device coupled to a fixed base. Typically, the positionable device can be coupled to one or more instruments to enable the instruments to be guided into the anatomy. As the positionable device can guide the instruments into the anatomy, it may be desirable to track the orientation of the positionable device relative to the anatomy. Further, it may be desirable to notify a user of the navigation system if the positionable device and/or the base is/are not properly aligned with the anatomy.

According to various embodiments, a system for positioning a guide relative to an anatomy is disclosed. The system can include a base adapted to be coupled to the anatomy, and a guide that can move relative to the base. The system can include at least one tracking device that can be coupled to the base and the guide, and a tracking system, which can track a position of the at least one tracking device relative to the anatomy. The system can include a navigation system, which can determine a position of the base and the guide relative to the anatomy based on the position of the at least one tracking device. The navigation system can also determine if the position of the base and the position of the guide are about equal to a desired position of the base and the movable member. The system can further include a display, which can display the desired position of the base and the guide superimposed on an image of the anatomy. The display can also display at least one icon superimposed on the image of the anatomy, which can graphically indicate a desired manipulation of the guide required to move the guide into the desired position for the guide relative to the anatomy.

Further disclosed is a method for positioning a guide relative to an anatomy. The method can include acquiring a surgical plan for a surgical procedure to be performed on the anatomy that includes a trajectory for an instrument. The method can also include tracking at least one first tracking device coupled to a base relative to the anatomy, and tracking at least one second tracking device coupled to a guide relative to the anatomy. The guide can also be movable relative to the base. The method can include determining a position of the base and guide relative to the anatomy. The method can also include comparing the position of the base and the guide relative to the anatomy with a desired position for the base and the guide in the surgical plan that enables the guide to guide the instrument along the trajectory. The method can include displaying at least one icon superimposed onto an image of the anatomy that indicates an amount and direction of a first manipulation required to move the guide into the desired position and at least one icon superimposed onto an image of the anatomy that indicates an amount and direction of a second manipulation required to move the guide relative to the base into the desired position.

Also disclosed is a system for positioning a reference frame relative to an anatomy. The system can include a base adapted to be fixedly coupled to the anatomy, and a guide that moves relative to the base. The guide can be operable to be coupled to a drive system to guide at least one instrument into the anatomy. The system can include at least one first tracking device coupled to the base, and at least one second tracking device coupled to the guide. The system can also include a tracking system, which can track a position of the at least one first tracking device and the at least one second device relative to the anatomy. The system can include a navigation control module, which can receive patient image data and surgical plan data. The surgical plan data can include a desired position for the base and the guide relative to the anatomy. The system can also include a navigation system, which can determine a position of the base and the guide relative to the anatomy based on the position of the at least one first tracking device and the at least one second tracking device. The navigation system can also determine if the position of the base and the position of the guide are about equal to the desired position of the base and the guide. The navigation control module can output image data that can include a first arrow icon superimposed onto the patient image data, which can graphically represent an amount of rotation and a direction of rotation for the guide, a second arrow icon superimposed onto the patient image data, which can graphically represent an amount of translation and a direction of translation for the guide, or combinations thereof.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 5 is a dataflow diagram illustrating a control system performed by a control module associated with the navigation system of FIG. 1; and FIG. 6 is a flowchart illustrating a control method performed by the control module.

DETAILED DESCRIPTION

Figure 1:
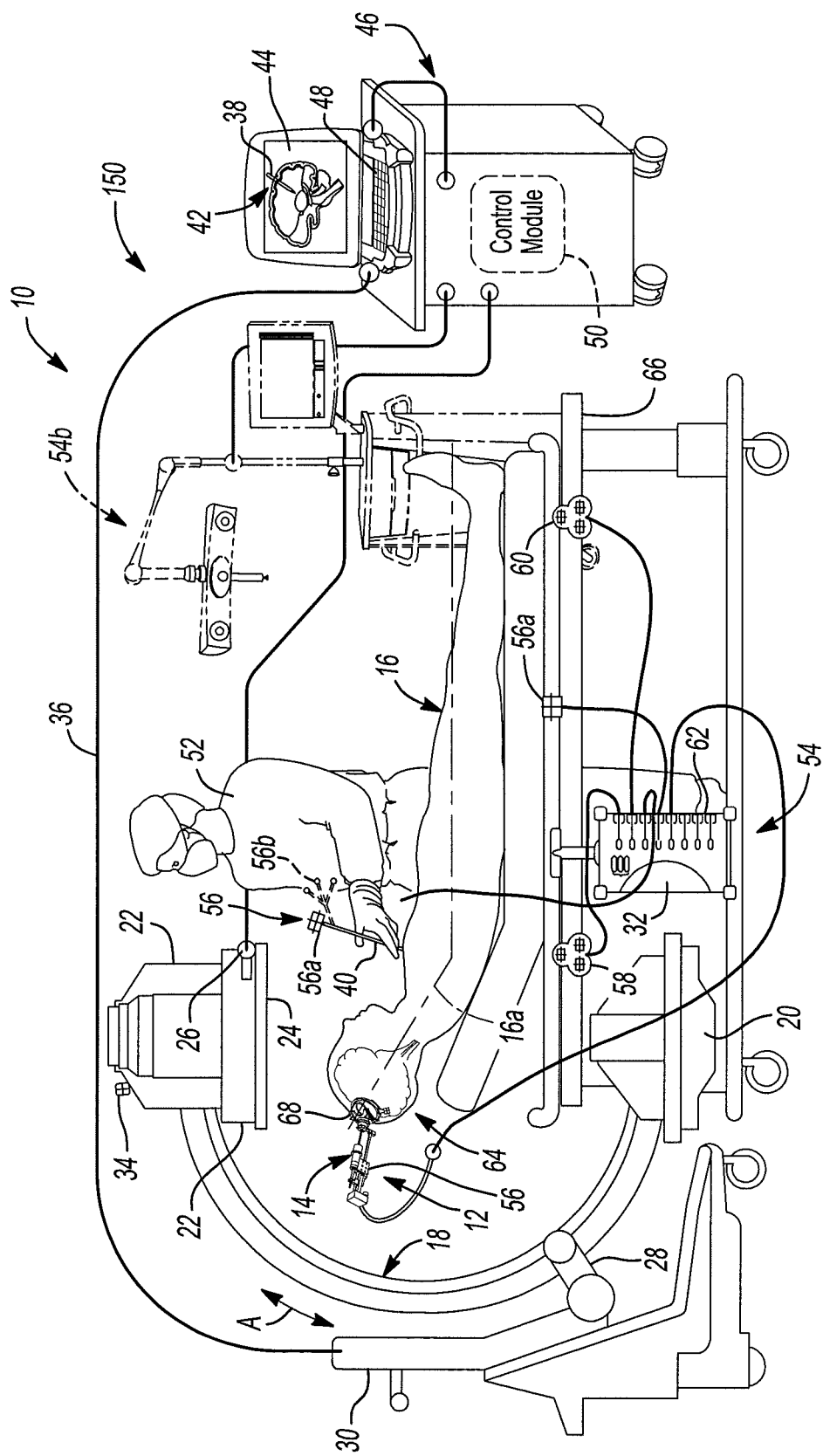
FIG. 1 is an environmental view of a surgical navigation system or computer aided surgical system, according to various embodiments.

The following description is merely exemplary in nature and is not intended to limit the present disclosure, application, or uses. It should be understood that throughout the drawings, corresponding reference numerals indicate like or corresponding parts and features. As indicated above, the present teachings are directed toward providing a system and method for positioning a reference frame for use in a navigated surgical procedure. It should be noted, however, that the present teachings could be applicable to any appropriate procedure in which it is desirable to assist a user in orientating a device within an operating theater, via a user interface. Further, as used herein, the term "module" can refer to an application specific integrated circuit (ASIC), an electronic circuit, a processor (shared, dedicated, or group) and memory that executes one or more software or firmware programs, a combinational logic circuit, and/or other suitable hardware or software, firmware programs or components that provide the described functionality. Therefore, it will be understood that the following discussions are not intended to limit the scope of the appended claims.

As will be discussed in greater detail herein, the present disclosure is directed toward a system and method for guiding a positioning of a reference frame relative to an anatomy, such as a brain, to facilitate a surgical procedure on the anatomy. In this regard, this system and method can include an exemplary surgical navigation system 10, which can include a drive system 12 to control the insertion and withdrawal of one or more instruments 14 from the anatomy. Various surgical navigation systems can include those described in U.S. patent application Ser. No. 10/651,267 (now U.S. Pat. App. Pub No. 2005/0049486), filed on Aug. 28, 2003, incorporated herein by reference. As will be discussed, the drive system 12 and the instruments 14 can be positioned relative to a dynamic reference frame, which can be coupled to a patient 16.

With reference to FIG. 1, the exemplary surgical navigation system 10 can include an image based system, an imageless system, an atlas or diagram based system, or combinations thereof. One skilled in the art will understand that the surgical navigation system 10 can require the registration of a patient 16, which defines patient space, to an image space, discussed further herein. According to various embodiments, registration can include registration between image space, defined by image data or atlas data, and the patient space.

With continued reference to FIG. 1, the navigation system 10 that can be used for various procedures is illustrated. The navigation system 10 can be used to track the location of an implant, such as a spinal implant or orthopedic implant, or a surgical device, such as an electrode, relative to a patient 16.

Also the navigation system 10 can track the position and orientation of various instruments 14. It should further be noted that the navigation system 10 may be used to navigate any type of instrument, implant, or delivery system, including: guide wires, arthroscopic systems, cardiac leads, orthopedic implants, spinal implants, deep-brain stimulator (DBS) probes, microelectrode recorder probes, macroelectrode stimulation probes, etc. Moreover, these instruments may be used to navigate or map any region of the body. The navigation system 10 and the various instruments may be used in any appropriate procedure, such as one that is generally minimally invasive, arthroscopic, percutaneous, stereotactic, or an open procedure.

Although an exemplary navigation system 10 that can include the imaging device 18 is discussed herein, one skilled in the art will understand that the disclosure is merely for clarity of the present discussion and any appropriate imaging system, navigation system, patient specific data, and non-patient specific data can be used. For example, the intraoperative imaging system can include an MRI imaging system, such as the PoleStar® MRI or an O-arm™ imaging system sold by Medtronic, Inc. It will be understood that the navigation system 10 can incorporate or be used with any appropriate preoperatively or intraoperatively acquired image data. For example, various imageless systems can be used or images from atlas models can be used to produce patient images, such as those disclosed in U.S. Patent Pub. No. 2005-0085714, filed Oct. 16, 2003, entitled "Method and Apparatus for Surgical Navigation of a Multiple Piece Construct for Implantation," incorporated herein by reference. The imaging device 18 can be, for example, a fluoroscopic x-ray imaging device that may be configured as an O-arm™ or a C-arm, which can have an x-ray source 20, an x-ray receiving section 22, an optional calibration and tracking target 24 and optional radiation sensors 26.

In operation, the imaging device 18 can generate x-rays from the x-ray source 20 that can propagate through the patient 16 and calibration and/or tracking target 24, into the x-ray receiving section 22. This allows direct visualization of the patient 16 and radio-opaque instruments in the cone of the X-rays. In the example of FIG. 1, a longitudinal axis 16a of the patient 16 is substantially in line with a mechanical axis 28 of the C-arm. This can enable the imaging device 18 to be rotated relative to the patient 16, allowing images of the patient 16 to be taken from multiple directions or about multiple planes. An example of a fluoroscopic C-arm X-ray device that may be used as the optional imaging device 18 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

When the x-ray source 20 generates the x-rays that propagate to the x-ray receiving section 22, the radiation sensors 26 can sense the presence of radiation, which is forwarded to an imaging device controller 30, to identify whether or not the imaging device 18 is actively imaging. This information can also be transmitted to a coil array controller 32, further discussed herein.

The imaging device controller 30 can capture the x-ray images received at the x-ray receiving section 22 and store the images for later use. Multiple two-dimensional images taken by the imaging device 18 may also be captured and assembled by the imaging device controller 30 to provide a larger view or image of a whole region of the patient 16, as opposed to being directed to only a portion of a region of the patient 16. The imaging device controller 30 may also be separate from the imaging device 18 and/or control the rotation of the imaging device 18. For example, a C-arm can move in the direction of arrow A or rotate about the longitudinal axis 16a of the patient 16, allowing anterior or lateral views of the patient 16 to be imaged. Each of these movements involves rotation about the mechanical axis 28 of the C-arm. The movements of the imaging device 18, such as the C-arm, can be tracked with a tracking device 34.

While the imaging device 18 is shown in FIG. 1 as a C-arm, any other alternative 2D, 3D or 4D imaging modality may also be used. For example, any 2D, 3D or 4D imaging device, such as the O-arm™ imaging device, isocentric fluoroscopy, bi-plane fluoroscopy, ultrasound, computed tomography (CT), multi-slice computed tomography (MSCT), magnetic resonance imaging (MRI), high frequency ultrasound (HFU), positron emission tomography (PET), optical coherence tomography (OCT), intra-vascular ultrasound (IVUS), ultrasound, intra-operative CT or MRI may also be used to acquire 2D, 3D or 4D pre- or post-operative and/or real-time images or patient image data 36 of the patient 16. For example, an intra-operative MRI system, may be used such as the PoleStar® MRI system sold by Medtronic, Inc.

In addition, image datasets from hybrid modalities, such as positron emission tomography (PET) combined with CT, or single photon emission computer tomography (SPECT) combined with CT, could also provide functional image data superimposed onto anatomical data to be used to confidently reach target sites within the patient 16. It should further be noted that the imaging device 18 as shown in FIG. 1, provides a virtual bi-plane image using a single-head C-arm fluoroscope as the imaging device 18 by simply rotating the C-arm about at least two planes, which could be orthogonal planes, to generate two-dimensional images that can be converted to three-dimensional volumetric images. By acquiring images in more than one plane, an icon 38 representing the location of the instrument 14, such as an impacter, stylet, reamer driver, taps, drill, deep-brain stimulator (DBS) probes, cardiac leads or other instrument, or implantable devices introduced and advanced in the patient 16, may be superimposed in more than one view and included in image data 42 displayed on a display 44.

If the imaging device 18 is employed, patient image data 36 can be forwarded from the imaging device controller 30 to a navigation computer and/or processor or workstation 46. It will also be understood that the patient image data 36 is not necessarily first retained in the imaging device controller 30, but may also be directly transmitted to the workstation 46. The workstation 46 can include the display 44, a user input device 48 and a control module 50. The workstation 46 can also include or be connected to an image processor, navigation processor, and memory to hold instruction and data. The workstation 46 can provide facilities for displaying the patient image data 36 as an image on the display 44, saving, digitally manipulating, or printing a hard copy image of the received patient image data 36.

The user input device 48 can comprise any device that can enable a user to interface with the workstation 46, such as a touchpad, touch pen, touch screen, keyboard, mouse, wireless mouse, or a combination thereof. The user input device 48 allows a physician or user 52 to provide inputs to control the imaging device 18, via the imaging device controller 30, adjust the display settings of the display 44, or control a tracking system 54, as further discussed herein. The control module 50 can determine the location of a dynamic reference frame (DRF) 64 (FIG. 2) with respect to the patient space, and can output image data 42 to the display 44 to assist in positioning the DRF 64.

With continuing reference to FIG. 1, the navigation system 10 can further include the electromagnetic navigation or tracking system 54. A representative electromagnetic navigation or tracking system 54 can include the AXIEM™ electromagnetic tracking system sold by Medtronic Navigation, Inc. The tracking system 54 can include a localizer, such as a first coil array 58 and/or second coil array 60, the coil array controller 32, a navigation probe interface 62, the device or instrument 14, a patient tracker or dynamic reference frame (DRF) 64, and one or more tracking devices 56. Other tracking systems can include an optical tracking system 54b, for example the StealthStation® Treon® and the StealthStation® Tria® both sold by Medtronic Navigation, Inc. Further, other tracking systems can be used that include acoustic, radiation, radar, infrared, etc., or hybrid systems, such as a system that includes components of both an electromagnetic and optical tracking system, etc. The drive system 12, the instrument 14 and the DRF 64 can each include tracking device(s) 56.

The tracking device 56 or any appropriate tracking device as discussed herein, can include both a sensor, a transmitter, or combinations thereof and can be indicated by the reference numeral 56. Further, the tracking device 56 can be wired or wireless to provide a signal or emitter or receive a signal from a system. For example, a tracking device 56a can include one or more electromagnetic coils, such as a tri-axial coil, to sense a field produced by the localizing coil array 58 or 60. One will understand that the tracking device(s) 56 can receive a signal, transmit a signal, or combinations thereof to provide information to the navigation system 10, which can be used to determine a location of the tracking device 56. The navigation system 10 can determine a position of the instrument 14 and the DRF 64 based on the location of the tracking device(s) 56 to allow for accurate navigation relative to the patient 16 in the patient space.

With regard to the optical localizer or tracking system 54b, the optical tracking system 54b can transmit and receive an optical signal, or combinations thereof. An optical tracking device 56b can be interconnected with the instrument 14, or other devices such as the DRF 64. As generally known, the optical tracking device 56b can reflect, transmit or receive an optical signal to/from the optical localizer or tracking system 54b that can be used in the navigation system 10 to navigate or track various elements. Therefore, one skilled in the art will understand, that the tracking device(s) 56 can be any appropriate tracking device to work with any one or multiple tracking systems.

The coil arrays 58, 60 can transmit signals that are received by the tracking device(s) 56. The tracking device(s) 56 can then transmit or receive signals based upon the transmitted or received signals from or to the coil arrays 58, 60. The coil arrays 58, 60 are shown attached to an operating table 66. It should be noted, however, that the coil arrays 58, 60 can also be positioned at any other location, as well and can also be positioned in the items being navigated. The coil arrays 58, 60 include a plurality of coils that are each operable to generate distinct electromagnetic fields into the navigation region of the patient 16, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil arrays 58, 60 can be controlled or driven by the coil array controller 32. The coil array controller 32 can drive each coil in the coil arrays 58, 60 in a time division multiplex or a frequency division multiplex manner. In this regard, each coil can be driven separately at a distinct time or all of the coils can be driven simultaneously with each being driven by a different frequency. Upon driving the coils in the coil arrays 58, 60 with the coil array controller 32, electromagnetic fields are generated within the patient 16 in the area where the medical procedure is being performed, which is again sometimes referred to as patient space. The electromagnetic fields generated in the patient space induce currents in a tracking device(s) 56 positioned on or in the drive system 12, the instrument 14 and the DRF 64. These induced signals from the drive system 12, the instrument 14 and the DRF 64 are delivered to the navigation probe interface 62 and can be subsequently forwarded to the coil array controller 32.

The navigation probe interface 62 may provide the necessary electrical isolation for the navigation system 10. The navigation probe interface 62 can also include amplifiers, filters and buffers to directly interface with the tracking device(s) 56 in the instrument 14 and DRF 64. Alternatively, the tracking device(s) 56, or any other appropriate portion, may employ a wireless communications channel, such as that disclosed in U.S. Pat. No. 6,474,341, entitled "Surgical Communication Power System," issued Nov. 5, 2002, incorporated herein by reference, as opposed to being coupled directly to the navigation probe interface 62.

Figure 2:
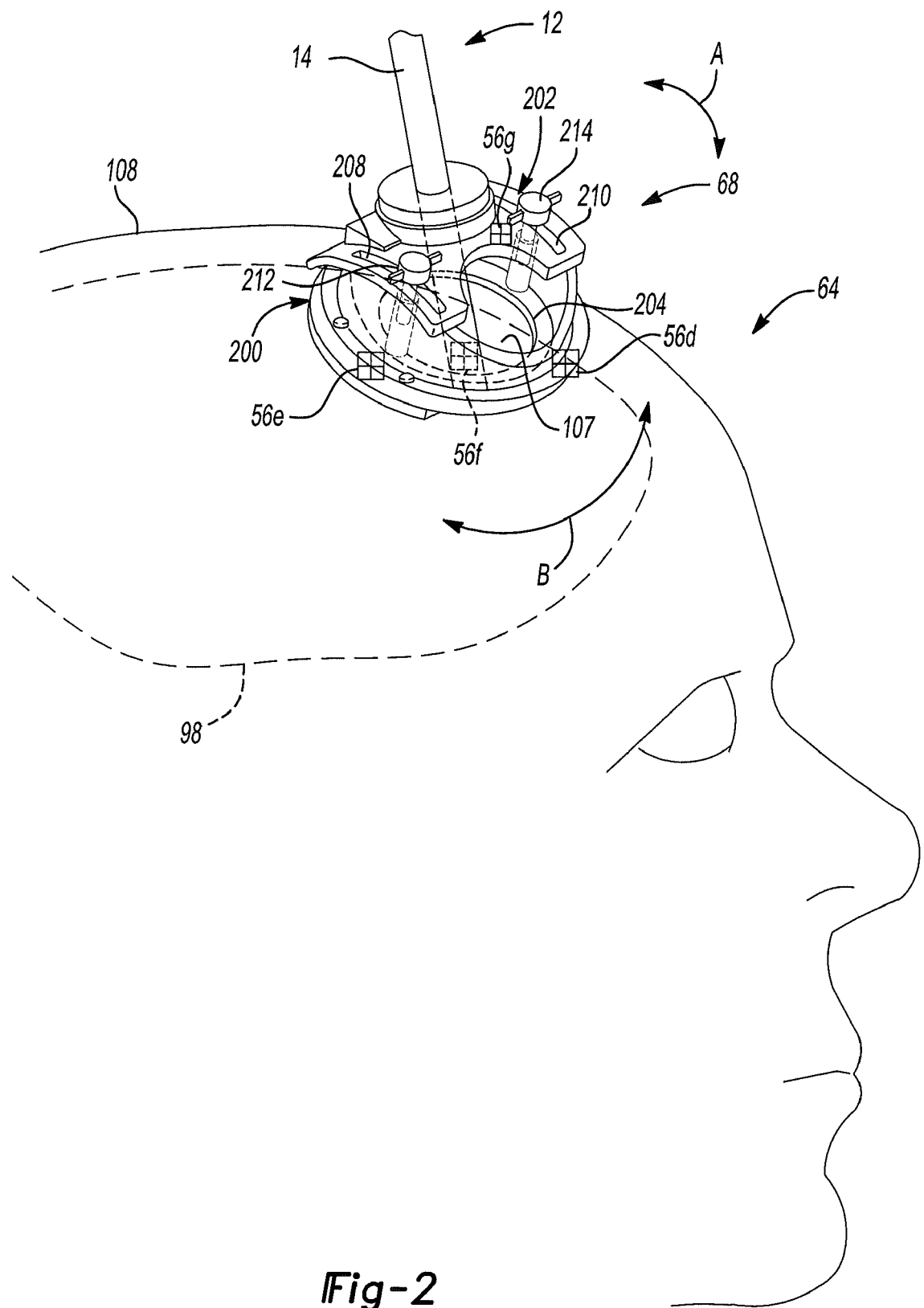
FIG. 2 is a detail environmental view of an exemplary dynamic reference frame (DRF) holder, for example, a head frame, for use with the navigation system of FIG. 1 according to various embodiments.

The instrument 14 may be any appropriate instrument, such as an instrument for preparing a portion of the patient 16, an instrument for recording activity in a portion of the anatomy or an instrument for positioning an implant. With reference to FIGS. 1 and 2, the DRF 64 may be fixed to the patient 16 adjacent to the region being navigated so that any movement of the patient 16 is detected as relative motion between the coil arrays 58, 60 and the DRF 64. This relative motion is forwarded to the coil array controller 32, which updates registration correlation and maintains accurate navigation, further discussed herein. The DRF 64 may include any appropriate tracking device 56 used by the navigation system 10. Therefore, the DRF 64 can include an electromagnetic tracking device, optical, acoustic, etc. Further, with reference to FIG. 2, the DRF 64 can include a DRF holder or head frame 68 and one or more tracking device(s) 56. Alternatively, the DRF 64 can include tracking device(s) 56 that can be formed integrally with the head frame 68.

Moreover, the DRF 64 can be provided as separate pieces and can be positioned at any appropriate position on the anatomy. For example, the tracking device(s) 56 of the DRF 64 can be fixed to the skin of the patient 16 with an adhesive. Also, the DRF 64 can be positioned near a leg, arm, etc. of the patient 16. Thus, the DRF 64 does not need to be provided with the head frame 68 or require any specific base or holding portion. If the DRF 64 is used with an electromagnetic tracking device 56a, it can be configured as a pair of orthogonally oriented coils, each having the same center or may be configured in any other non-coaxial or co-axial coil configurations, such as a tri-axial coil configuration (not specifically shown).

Briefly, the navigation system 10 operates as follows. The navigation system 10 creates a translation map between all points in the radiological image generated from the imaging device 18 in image space and the corresponding points in the anatomical structure of the patient 16 in patient space. After this map is established, whenever a tracked instrument, such as the instrument 14 is used, the workstation 46 in combination with the coil array controller 32 and the imaging device controller 30 uses the translation map to identify the corresponding point on the pre-acquired image or atlas model, which is displayed on display 44. This identification is known as navigation or localization. The icon 38 representing the localized point or instruments 14 can be shown as image data 42 on the display 44.

To enable navigation, the navigation system 10 must be able to detect both the position of the anatomical structure of the patient 16 and the position of the instrument 14. Knowing the location of these two items allows the navigation system 10 to compute and display the position of the instrument 14 in relation to the patient 16 on the display 44. The tracking system 54 can be employed to track the instrument 14 and the anatomical structure simultaneously.

The tracking system 54, if using an electromagnetic tracking assembly, essentially works by positioning the coil arrays 58, 60 adjacent to the patient space to generate a low-energy electromagnetic field generally referred to as a navigation field. Because every point in the navigation field or patient space is associated with a unique field strength, the tracking system 54 can determine the position of the instrument 14 by measuring the field strength at the tracking device 56 location. The DRF 64 can be fixed to the patient 16 to identify a first location of the patient 16 in the navigation field. The tracking system 54 can continuously recompute the relative position of the DRF 64 and the instrument 14 during localization and relate this spatial information to patient registration data to enable image guidance of the instrument 14 within and/or relative to the patient 16.

Patient registration is the process of determining how to correlate the position of the drive system 12 and/or the instrument 14 relative to the patient 16 to the position on the diagnostic or pre-acquired images. To register the patient 16, a physician or user 52 may use point registration by selecting and storing particular points from the pre-acquired images and then touching the corresponding points on the anatomical structure of the patient 16 with a tracked pointer probe 40. The navigation system 10 analyzes the relationship between the two sets of points that are selected and computes a match, which correlates every point in the patient image data 36 with its corresponding point on the anatomical structure of the patient 16 or the patient space, as discussed herein. The points that are selected to perform registration are fiducial markers, such as anatomical landmarks. Again, the landmarks or fiducial markers are identifiable on the images and identifiable and accessible on the patient 16. The fiducial markers can be artificial markers that are positioned on the patient 16 or anatomical landmarks that can be easily identified in the patient image data 36. The artificial landmarks, such as the fiducial markers, can also form part of the DRF 64, such as those disclosed in U.S. Pat. No. 6,381,485, entitled "Registration of Human Anatomy Integrated for Electromagnetic Localization," issued Apr. 30, 2002, herein incorporated by reference.

The navigation system 10 may also perform registration using anatomic surface information or path information as is known in the art. The navigation system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 10/644,680, entitled "Method and Apparatus for Performing 2D to 3D Registration" filed on Aug. 20, 2003, hereby incorporated by reference.

In order to maintain registration accuracy, the navigation system 10 continuously tracks the position of the patient 16 during registration and navigation. This is because the patient 16, DRF 64 and coil arrays 58, 60 may all move during the procedure, even when this movement is not desired. Therefore, if the navigation system 10 did not track the position of the patient 16 or area of the anatomy, any patient movement after image acquisition would result in inaccurate navigation within that image. Because the DRF 64 can be coupled to the patient 16, any movement of the anatomical structure of the patient 16 or the coil arrays 58, 60 can be detected as the relative motion between the coil arrays 58, 60 and the DRF 64. Both the relative motion of the coil arrays 58, 60 and the DRF 64 can be communicated to the coil array controller 32, via the navigation probe interface 62, which can update the registration correlation to thereby maintain accurate navigation.

With continued reference to FIG. 1 and with additional reference to FIG. 2, the guide or drive system 12 for use with an exemplary head frame 68, such as a stereotactic head frame or a small scale sterotactic head frame 68 is illustrated. The drive system 12 can be used to drive various instruments, such as one or more instruments 14, such as electrodes, into an anatomy, such as a brain 98. For example, a procedure on the brain 98 can include a recorder for detecting electrical activity in the brain 98 with a microelectrode (ME) or macroelectrode. Once a recording of the brain 98 has occurred, a stimulator probe, such as a deep brain stimulator probe or a macroelectrode can be delivered to an area identified with the ME or macroelectrode. Generally, the ME or macroelectrode, after identifying an area of interest in the brain 98, can be removed and the stimulator probe can be driven and guided along a similar or identical trajectory or axis relative to the removed ME or macroelectrode. The stimulator probe can be provided to electrically stimulate the selected region of the anatomy, either short term or long term.

With reference to FIG. 2, the drive system 12 can include any appropriate drive system. For example, the drive system 12 can comprise the microtargeting Drive® system produced by Fred Haer Corp., FHC Inc. of 9 Main Street, Bowdoinham Me. 04008, USA. The drive system 12 can be interconnected with various guide or support portions, such as the stereotactic head frame, the small-scale head frame 68, robotic devices, or guide devices, to drive various instruments into selected portions of the anatomy. For example, the stereotactic head frame can comprise any suitable stereotactic head frame known in the art, such as the Leksell Stereotactic System® provided by Elekta AB, and the small-scale head frame 68 can be any appropriate mechanism, such as the NEXFRAME™ sold by Medtronic Image Guided Neurologics of Minnesota, USA. The drive system 12 can be interconnected with the head frames 68 to position the drive system 12 at any appropriate location to drive various instruments 14 into a cranium 108. The drive system 12 can also include one or more tracking devices 56 (FIG. 1), which can be used with the navigation system 10 to determine a position of the drive system 12 relative to the patient 16.

With continued reference to FIG. 2, the head frame 68 can be positioned about an entry point, such as a burr hole 107, formed in the cranium 108. The head frame 68 can include various portions, but generally includes a base 200, a trajectory guide portion, movable portion, saddle or guide 202 and one or more tracking devices 56, which are generally referred to by reference numeral 56. The base 200 can define an aperture or opening 204 that allows the instruments 14 to pass through the base 200 into the cranium 108. One or more bone screws can be used to fix the base 200 relative to the patient 16. The trajectory guide portion, moveable base or guide 202 can be interconnected to the base 200 and the drive system 12 can be connected to the guide 202.

The guide 202 can move relative to the base 200 via a track or slot 208, 210 defined by the guide 202. The guide 202 can be guided or navigated to a selected location or orientation relative to the opening 204, which in turn, can align the drive system 12 into a selected location or orientation relative to the patient 16. The guide 202 can then be fixed in place via any appropriate mechanism, such as one or more locking screws 212, 214. Various markings can be provided on the guide 202 or the fixed base 200 to assist in obtaining a selected orientation of the guide 202 to the cranium 108.

For example, the guide 202 may be allowed to move through a predefined range of motion relative to the base 200. In a further example, the slots 208, 210 can be angled relative to the base 200, and the guide 202 can move or slide in an arcuate manner relative to the base 200 from about 30 to about 60 degrees relative to the base 200, as indicated by the arrow A in FIG. 2. In one example, the guide 202 can also rotate relative to the base 200, and thus, the anatomy. For example, the guide 202 can rotate about 360 degrees relative to the base 200, as indicated by the arrow B. As the guide 202 can move relative to the base 200, and thus, the patient 16, the guide 202 may limit to the amount of trajectory of the instrument 14 can achieve relative to the patient 16 from any one location of the guide 202. Thus, the position of the guide 202 relative to the patient 16 can ensure an appropriate trajectory can be aligned with the instrument 14.

The tracking devices 56 can be interconnected to the base 200 and the guide 202. For example, the base 200 can include a first tracking device 56d, which can be fixed to or positioned within the base 200. Optionally, the base 200 can include a second tracking device 56e and a third tracking device 56f. The guide 202 can include a fourth tracking device 56g, which can be fixed to or positioned within the guide 202. The tracking devices 56d-g can enable the tracking system 54 to track the position of the base 200 and the guide 202. It will be understood that the number of tracking devices 56 coupled to the base 200 and the guide 202 are merely exemplary, and any suitable number of tracking devices 56 can be coupled to the base 200 and guide 202.

The tracking devices 56d-g can comprise the electromagnetic tracking device 56a for use with the electromagnetic tracking system 54, the optical tracking device 56b for use with the optical tracking system 54a, or a combination thereof. If the tracking devices 56d-g comprise electromagnetic tracking devices 56a, the tracking devices 56d-g can also be used as field generating electromagnetic coils for various reasons, such as guiding the instrument 14. Thus, the tracking devices 56d-g can both generate a field and receive or sense a field generated by other electromagnetic coils, similar to the coils of the coil arrays 58, 60. It will also be understood, that in the case of electromagnetic tracking devices, the first tracking device 56d can either sense a field generated by another coil array 58, 60 or the first tracking device 56d can transmit a field to be sensed by the coil arrays 58, 60. In either case, the position of the first tracking device 56d in the base 200 can be determined and this determination can be used for navigation of the base 200. Similar methods can be applied to any other electromagnetic tracking devices 56, such as those on the guide 202, according to various embodiments. The various tracking devices 56d-g can be used with the navigation system 10, to determine a position of the various components of the head frame 68 or the drive system 12 relative the cranium 108, as further discussed herein. In addition, it will be understood that the use of tracking devices 56d-g is merely exemplary, as any suitable mechanism could be employed to position the head frame 68, such as fluoroscopy, for example.

As the base 200 can be fixed relative to the patient 16, the tracking devices 56 associated with the base 200 can be fixed relative to the patient 16, and thus, can form a dynamic reference frame. Moreover, the tracking devices 56 coupled to the base 200 can generate an electromagnetic field, which can be utilized during a portion of a procedure, such as for guiding the instrument 14. Additional detail regarding the placement and use of tracking devices 56 with the head frame 68 is disclosed in U.S. patent Ser. No. 12/110,666, entitled "Method and Apparatus for Performing a Navigated Procedure," which is hereby incorporated by reference herein in its entirety.

The head frame 68 can be positioned on the patient 16 according to a plan or at a predetermined location. As discussed above, the patient image data 36 can be acquired of the patient 16 including the cranium 108. The patient image data 36 or any appropriate portion can be used with the workstation 46 to plan or predetermine the location for the head frame 68. Then, the navigation system 10 can be used to navigate and track the position of the head frame 68 relative to the patient 16 and the predetermined location for the head frame 68, as discussed further herein. The position of the head frame 68 can be displayed on the display 44 relative to the image data 42, which can include an image of the cranium 108, and instructions on how to position the head frame 68, as will be discussed.

Figure 3:
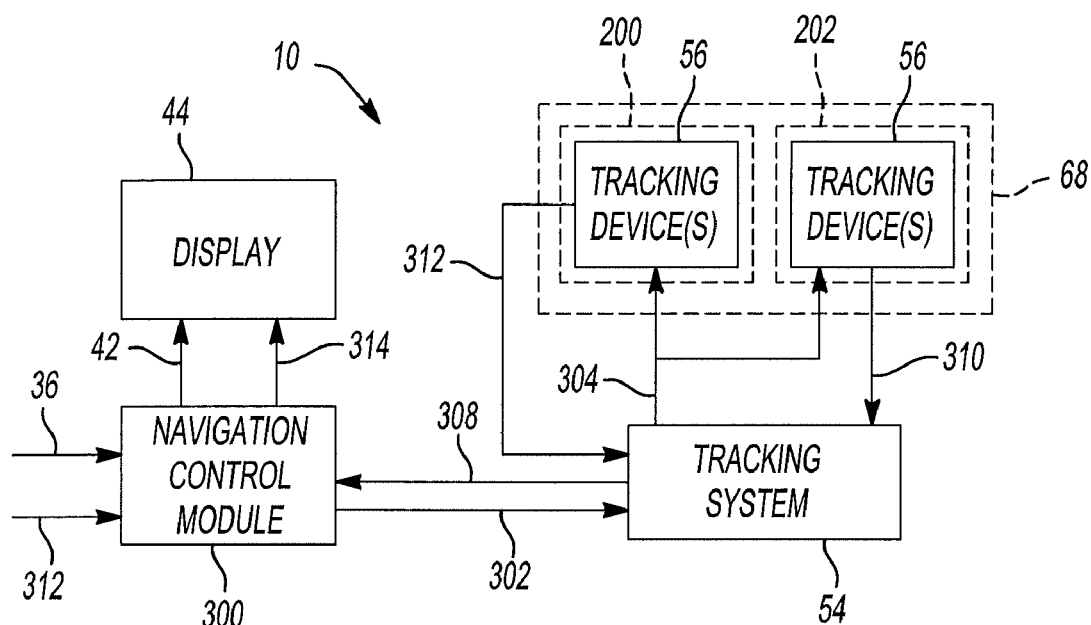
FIG. 3 is a simplified block diagram illustrating the navigation system of FIG. 1.

With reference now to FIG. 3, a simplified block diagram schematically illustrates an exemplary navigation system 10 for implementing the control module 50. The navigation system 10 can include the tracking system 54, the head frame 68, a navigation control module 300 and the display 44. The navigation control module 300 can form a portion of the control module 50. The head frame 68 can include the base 200 and the guide 202. Each of the base 200 and the guide 202 can include the tracking device(s) 56.

The tracking system 54 can comprise the electromagnetic tracking system 54 or the optical tracking system 54b, and will generally be referred to as the tracking system 54. The tracking system 54 can receive start-up data 302 from the navigation control module 300. In the case of an electromagnetic tracking system 54, based on the start-up data 302, the tracking system 54 can set activation signal data 304 that can activate or drive the coil arrays 58, 60 to generate an electromagnetic field to which the tracking device(s) 56 coupled to the head frame 68 can receive. The tracking system 54 can also set tracking data 308 for the navigation control module 300, as will be discussed. The tracking data 308 can include data regarding the location or position of the tracking device(s) 56 coupled to the head frame 68 in the patient space as computed from data received from the tracking device(s) 56 or sensor data 310.

When the tracking device(s) 56 receive the electromagnetic field generated by the coil arrays 58, 60, the tracking device(s) 56 can transmit sensor data 310 indicative of a position of the tracking device 56 in the patient space to the tracking system 54. Based on the sensor data 310 received by the tracking system 54, the tracking system 54 can generate and set the tracking data 308 for the navigation control module 300.

The navigation control module 300 can receive the tracking data 308 from the tracking system 54. The navigation control module 300 can also receive patient image data 36 and plan data 312 as input. The patient image data 36 can comprise images of the anatomical structure of the patient 16 obtained from a pre- or intra-operative imaging device, such as the images obtained by the imaging device 18. The plan data 312 can comprise a trajectory for the instrument 14, which can be entered by the user 52, via the workstation 46, or could be loaded onto the workstation 46 from a portable electronic device, such as a portable data device.

Based on the tracking data 308, the patient image data 36 and the plan data 312, the navigation control module 300 can generate image data 42 for display on the display 44. The image data 42 can comprise the patient image data 36 superimposed with an icon 316 of the head frame 68 and a target 318 identified from the plan data 312. The image data 42 can also include a substantially real-time indication of the position and orientation of the head frame 68 in patient space, as indicated by at least one directional icon 315, shown in FIG. 4. The image data 42 could also comprise a schematic illustration of the instrument 14 within the anatomical structure of the patient 16, as shown in FIG. 1, or the icon 38 of the instrument 14 superimposed on the patient image data 36, etc.

Figure 4:
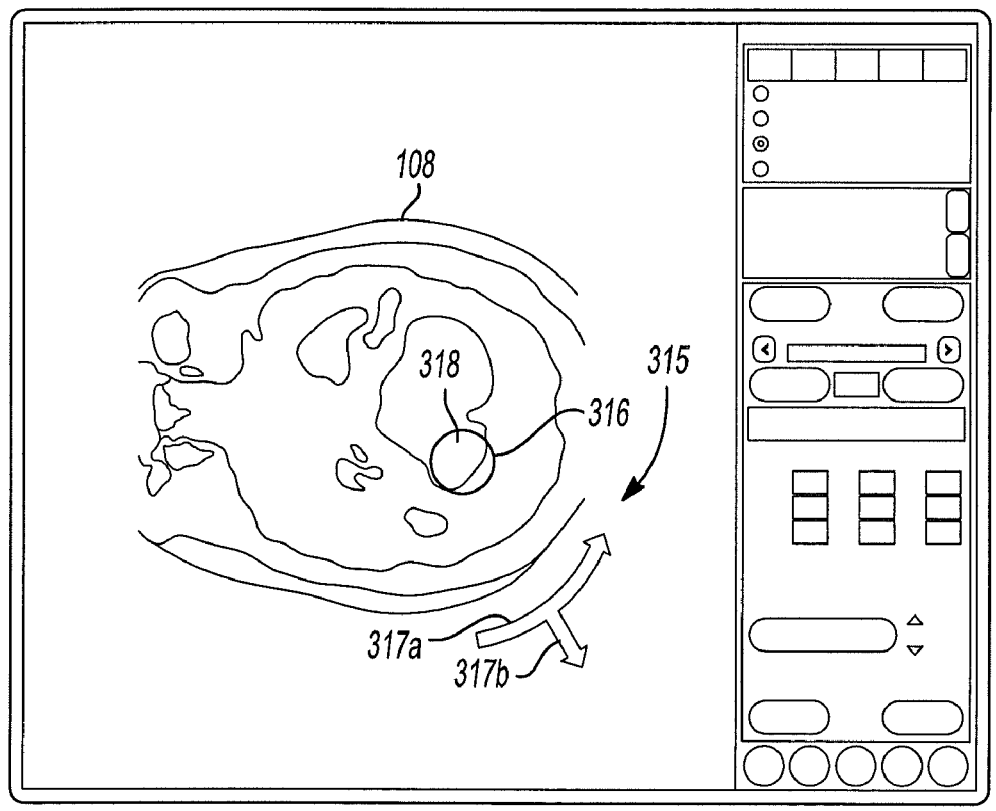
FIG. 4 is a graphical representation of an exemplary display produced by the navigation system of FIG. 1.

For example, as shown in FIG. 4, the at least one directional icon 315 can comprise one or more arrows 317. For example, a first arrow 317a can denote a desired movement of the base 200 to align the base 200 relative to the anatomy such as the cranium 108, and a second arrow 317b can denote a desired movement of the guide 202 to align the guide 202 relative to the anatomy, in accordance with the surgical plan outlined in the plan data 312. In this regard, as the trajectory of the instrument 14 can be defined by the guide 202, the guide 202 and the base 200 need to be properly aligned in accordance with the plan data 312 to ensure the instrument 14 can reach the target 318, via the trajectory outlined in the surgical plan. By providing the at least one directional icon 315, the user 52 can easily determine how to move the base 200 and/or guide 202 relative to the anatomy and to each other to execute the surgical plan.

In one example, with reference to FIGS. 2 and 4, the user 52 can position the base 200 onto the cranium 108. When the position of the base 200 relative to the anatomy corresponds to the desired position of the base 200 denoted in the surgical plan, one or more bone screws can be used to couple the base 200 to the anatomy (FIG. 2). Next, the arrow 317a can indicate a desired amount and direction of rotation for the guide 202 about a first axis relative to the anatomy. Once the guide 202 has reached the desired position, the arrow 317a can diminish or disappear, thereby indicating that no additional rotation of the guide 202 is necessary. Then, the guide 202 can be coupled to the base 200, such that the slides 208, 210 can move the guide 202 about a second axis relative to the base 200 (FIG. 2). Based on the position of the guide 202 relative to the anatomy, the arrow 317b can indicate a desired movement or translation of the guide 202 relative to the base 200. Once the guide 202 has reached the desired position based on the surgical plan, the arrow 317b can diminish and the locking screws 212, 214 (FIG. 2) can be tightened to couple the guide 202 relative to the base 200 and the anatomy.

In addition, the at least one directional icon 315 can reduce in size as the base 200 and/or guide 202 reach their respective desired position relative to the anatomy and each other, which can further assure the user 52 that the head frame 68 is properly aligned relative to the anatomy. It should be noted, however, that although the at least one direction icon 315 is described and illustrated herein as comprising one or more arrows 317, the at least one directional icon 315 could comprise any suitable means to notify the user 52 of the necessary movement of the head frame 68 relative to the anatomy, such as a dialogue box, pop-up message, text, graphical representation of the desired final alignment, etc. Further, although the at least one directional icon 315 is described herein as reducing in size as the user 52 approaches the desired orientation for the head frame 68, any other suitable notification means could be employed, such as a change in color, pop-up message, audible signal, text, etc.

With reference now to FIG. 5, a dataflow diagram illustrates an exemplary control system that can be embedded within the control module 50. Various embodiments of the control system according to the present disclosure can include any number of sub-modules embedded within the control module 50. The sub-modules shown may be combined and/or further partitioned to similarly determine the orientation or position of the head frame 68 within the patient space based on the signals generated by the tracking device(s) 56. In various embodiments, the control module 50 includes the tracking system 54 that can implement a tracking control module 320, and the workstation 46 that can implement the navigation control module 300. It should be noted, however, that the tracking control module 320 and the navigation control module 300 could be implemented on the workstation 46, if desired.

The tracking control module 320 can receive as input the start-up data 302 from the navigation control module 300 and sensor data 310 from the tracking device(s) 56. Upon receipt of the start-up data 302, the tracking control module 320 can output the activation signal data 304 for the tracking device(s) 56. Upon receipt of the sensor data 310, the tracking control module 320 can set the tracking data 308 for the navigation control module 300. As discussed, the tracking data 308 can include data regarding the positions of the base 200 and the guide 202.

The navigation control module 300 can receive as input the tracking data 308, the patient image data 36 and the plan data 312. Based on the tracking data 308 and the plan data 312, the navigation control module 300 can determine the appropriate patient image data 36 for display on the display 44, and can output the tracking data 308, the plan data 312 and the patient image data 36 as image data 42. Further, the navigation control module 300 can output notification data 314 to the display 44 if the position of the head frame 68 does not correspond with the plan data 312. The notification data 314 can comprise the at least one directional icon 315.

With reference now to FIG. 6, a flowchart diagram illustrates an exemplary method performed by the control module 50. At block 400, the method can acquire the plan data 312. The plan data 312 can be acquired by the workstation 46 from an input from the user 52, but could be acquired from another control module. At block 402, the method can determine a desired position for the head frame 68 based on the plan data 312. At block 404, the method can determine the actual position of the head frame 68 based on the tracking data 308 received from the tracking device(s) 56. At decision block 406, the method can determine if the actual position of the head frame 68 is about equal to the desired position of the head frame 68. If the actual position of the headframe 68 is about equal to the desired position of the headframe 68, then the method can end.

Otherwise, at block 408, the method can output image data 42, which can include icon(s), such as the at least one directional icon 315, that can indicate a movement or manipulation of the headframe 68 required for the headframe 68 to reach the desired position. For example, the at least one directional icon 315 can indicate a desired rotation of the guide 202 or translation of the guide 202. Next, the method can go to block 404.

Therefore, the control module 50 of the present disclosure can provide a user 52, such as a surgeon, with an accurate representation of the position and orientation of the head frame 68, within the patient space to enable the user 52 to orientate the head frame 68 prior to the surgical procedure. In this regard, the use of the tracking device(s) 56 on the head frame 68 can enable an accurate depiction on the display 44 of the position of the head frame 68 relative to the anatomical structure of the patient 16. The use of the tracking device(s) 56 in combination with the at least one directional icon 315, can enable the display 44 to graphically indicate a desired manipulation or movement for the head frame 68 to easily enable the user 52 to align the head frame 68 in the desired position. As the head frame 68 in some instances can be used to guide the instrument(s) 14 into the anatomy, the proper alignment of the head frame 68 relative to the anatomy can ensure the instrument(s) 14 can be guided to reach the desired target within the anatomy.

One skilled in the art will understand that the processes and systems discussed above can be used in a surgical procedure. The processes and systems, however, are understood to not be limited to use during or with a surgical procedure. The systems and processes can be used to acquire information regarding inanimate objects, inform or build a database of information; plan a procedure; formulate teaching aids, etc. Registration of image space to physical space can be performed relative to any object in physical space, including a patient, an inanimate object, etc. Also, the registration can occur for any appropriate reason, which may or may not be a surgical procedure.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

For example, while the navigation system 10 has been described as displaying the at least one directional icon 315, those of skill in the art will appreciate that the present disclosure, in its broadest aspects, may be constructed somewhat differently. In this regard, the navigation system 10 could use one or more audible cues to guide the user 52 in the movement or manipulation of the head frame 68. For example, the audible cues could increase as the user 52 reaches the desired position for the head frame 68.

What is claimed is:

1. A system for positioning a guide relative to an anatomy comprising:
   a base adapted to be moved relative to the anatomy and thereafter immoveably coupled to the anatomy;
   a guide moveably coupled to the base, wherein the guide is configured to move relative to the base at least when the base is immoveably coupled to the anatomy;

a first tracking device coupled to the base and a second tracking device coupled to the guide;

a tracking system that tracks a position of the first tracking device and the second tracking device relative to the anatomy;

a navigation system configured to independently determine a position of both the base and the guide relative to the anatomy based on the position of the first tracking device and the second tracking device and determine if the determined position of the base and the determined position of the guide are about equal to a desired position of the base and a desired position of the guide; and a display configured to display the desired position of the base and the guide superimposed on an image of the anatomy, a first directional icon superimposed on the image of the anatomy that graphically indicates a desired manipulation of the base required to move the base into the desired position of the base relative to the anatomy and a second directional icon superimposed on the image of the anatomy that graphically indicates a desired manipulation of the guide required to move the guide into the desired position of the guide relative to the anatomy.

2. The system of claim 1, wherein the desired position of the base and the desired position the guide relative to the anatomy are both predetermined from a surgical plan.

3. The system of claim 2, wherein the base and the guide each define a central bore, and the system further comprises:
at least one instrument movable through the central bore of the base and the guide to perform a procedure on the anatomy.

4. The system of claim 3, wherein the surgical plan includes a target site within the anatomy for the at least one instrument to perform the procedure, and the desired position of the base and the desired position the guide is aligned with a trajectory for the at least one instrument to travel to reach the target site.

5. The system of claim 1, wherein the image of the anatomy is acquired by an imaging device selected from at least one of a fluoroscopy device, an O-arm device, a bi-plane fluoroscopy device, an ultrasound device, a computed tomography (CT) device, a multi-slice computed tomography (MSCT) device, a magnetic resonance imaging (MRI) device, a high frequency ultrasound (HFU) device, a positron emission tomography (PET) device, an optical coherence tomography (OCT) device, an intra-vascular ultrasound (IVUS) device, an intra-operative CT device, an intra-operative MRI device or combinations thereof.

6. The system of claim 1, wherein the target site is selected from at least one of a surgical site, an anatomical site, a navigation area and combinations thereof.

7. The system of claim 1, wherein the first tracking device comprises at least one optical tracking device to track at least one degree of freedom information.

8. The system of claim 1, wherein the first tracking device and the second tracking device comprises at least one electromagnetic tracking device selected from the group including: an electromagnetic receiver tracking device, an electromagnetic transmitter tracking device or combinations thereof.

9. The system of claim 1, wherein the guide is rotatable relative to the anatomy.

10. The system of claim 9, wherein the first directional icon includes a third arrow that graphically represents an amount of rotation and a direction of rotation for the base, a second arrow that graphically represents an amount of translation and a direction of translation for the base, or combinations thereof;
wherein the second directional icon includes a first arrow that graphically represents an amount of rotation and a direction of rotation for the guide, a second arrow that graphically represents an amount of translation and a direction of translation for the guide, or combinations thereof.

11. The system of claim 4, wherein based on the surgical plan, the navigation system displays the second directional icon as a first arrow and a second arrow that indicates an alignment for the guide to allow the instrument to follow a trajectory through the base and the guide.

12. A method for positioning a guide relative to an anatomy comprising:
acquiring a surgical plan for a surgical procedure to be performed on the anatomy that includes a trajectory for an instrument;
tracking a first tracking device coupled to a base relative to the anatomy;
tracking a second tracking device coupled to a guide relative to the anatomy, the guide movable relative to the base;
determining a position of the base and guide relative to the anatomy;
comparing the position of the base and the guide relative to the anatomy with a desired base position for the base and a desired guide position for the guide in the surgical plan that enables the guide to guide the instrument along the trajectory; and
displaying at least a first icon superimposed onto an image of the anatomy that indicates an amount and direction of a first manipulation required to move the guide into the desired position and at least a second icon superimposed onto an image of the anatomy that indicates an amount and direction of a second manipulation required to move the guide relative to the base into the desired position.

13. The method of claim 12, further comprising:
moving the guide within a track defined on the guide relative to the base.

14. The method of claim 12, further comprising:
tracking a position of the base;
displaying a third icon superimposed onto an image of the anatomy that indicates an amount and direction of a third manipulation required to move the base into the desired base position;
coupling the base to the anatomy with at least one bone screw when the base is in the desired base position; and
coupling the guide to the base with at least one locking screw to immoveably fix the guide relative to the base when the guide is in the desired position.

15. The method of claim 12, further comprising:
superimposing an icon representing the base onto the image of the anatomy.

16. The method of claim 12 wherein the displayed at least first icon reduces in size as the guide approaches the desired location during the first manipulation, wherein the displayed at least second icon reduces in size as the guide approaches the desired location during the second manipulation, or combinations thereof.

17. A system for positioning a guide relative to an anatomy comprising:
a base adapted to be fixedly coupled at a selected location to the anatomy;

a guide that moves relative to the base to guide at least one instrument into the anatomy, the guide operable to be coupled to a drive system;
a first tracking device coupled to the base;
a second tracking device coupled to the guide;
a tracking system that tracks a position of the first tracking device and a position of the second device relative to the anatomy;
a navigation control module that receives patient image data and surgical plan data, the surgical plan data including a desired base position for the base and a desired guide position for the guide relative to the anatomy;
a navigation system that determines a position of the base and the guide relative to the anatomy based on the position of the first tracking device and the second tracking device, and determines if both the position of the base is about equal to the desired base position and if the position of the guide is about equal to the desired guide position; and
wherein the navigation control module outputs image data that includes:
a first arrow icon superimposed onto the patient image data that graphically represents an amount of movement required to move the base to the desired base position,
a second arrow icon superimposed onto the patient image data that graphically represents an amount of rotation and a direction of rotation for the guide to move the guide to the desired guide position, and
a third arrow icon superimposed onto the patient image data that graphically represents an amount of translation and a direction of translation for the guide to move the guide to the desired guide position, or combinations thereof.

18. The system of claim 17, further comprising:
a display that displays the image data.

19. The system of claim 17, wherein the surgical plan data includes a target site within the anatomy, and the image data further comprises an icon of the target site superimposed onto the patient image data.

20. The system of claim 17, wherein the first arrow icon reduces in size as the base approaches the desired position;
wherein the second arrow icon and the third arrow icon also reduce in size as the guide approaches the desired position.

21. The system of claim 1, wherein at least one of the first directional icon or the second directional icon includes at least one of a change in color, a pop-up message, an audible signal, or a text display.

22. The system of claim 1, further comprising:
a drive system coupled to the guide to be moved to a selected location and/or orientation relative to the anatomy by movement of the guide.

23. The system of claim 10, wherein the base is moveable independently of the guide and the first directional icon illustrates a direction of movement of the base to reach the desired base position independent of movement of the guide;
wherein the first directional icon and the second directional icon are the same icon and shown sequentially regarding movement of the base or movement of the guide.

24. The system of claim 10, wherein the first directional icon is removed when the base reaches the desired base position and the second directional icon is removed when the guide reaches the desired guide position.

25. The method of claim 12, wherein at least one of the first icon or the second icon diminishes or disappears as the guide moves towards the desired guide position, and
wherein the third icon diminishes or disappears as the base moves towards the desired base position.

26. The method of claim 14, wherein the base is moved independently of moving the guide;
wherein the base is coupled to the anatomy prior to coupling the guide to the base.

* * * * *